United States Patent [19]

Baker et al.

[11] Patent Number: 5,282,862
[45] Date of Patent: * Feb. 1, 1994

[54] SPINAL IMPLANT SYSTEM AND A METHOD FOR INSTALLING THE IMPLANT ONTO A VERTEBRAL COLUMN

[75] Inventors: Gregg S. Baker, Lake Forest; Paul B. Hafeli, El Toro, both of Calif.

[73] Assignee: Artifex Ltd., Newport Beach, Calif.

[*] Notice: The portion of the term of this patent subsequent to Jun. 29, 2010 has been disclaimed.

[21] Appl. No.: 802,009

[22] Filed: Dec. 3, 1991

[51] Int. Cl.⁵ .................... A61F 2/44; A61F 5/04
[52] U.S. Cl. ......................... 623/17; 606/60; 606/61
[58] Field of Search .............. 623/17; 606/60, 61

[56] References Cited

U.S. PATENT DOCUMENTS

| | | |
|---|---|---|
| 2,774,350 | 12/1956 | Cleveland, Jr. . |
| 3,242,922 | 3/1966 | Thomas . |
| 3,987,499 | 10/1976 | Scharbach et al. . |
| 4,636,217 | 1/1987 | Ogilvie et al. . |
| 4,648,388 | 3/1987 | Steffee . |
| 4,655,199 | 4/1987 | Steffee . |
| 4,696,290 | 9/1987 | Steffee . |
| 4,719,905 | 1/1988 | Steffee . |
| 4,771,767 | 9/1988 | Steffee . |
| 4,820,305 | 4/1989 | Harms et al. . |
| 4,836,196 | 6/1989 | Park et al. ............ 128/92 YM |
| 4,854,304 | 8/1989 | Zielke . |
| 4,854,311 | 8/1989 | Steffee . |
| 4,878,915 | 11/1989 | Brantigan . |
| 4,887,595 | 12/1989 | Heinig et al. . |
| 4,946,458 | 8/1990 | Harms et al. . |
| 4,987,892 | 1/1991 | Krag et al. . |
| 5,002,542 | 3/1991 | Frigg . |
| 5,005,562 | 4/1991 | Cotrel . |
| 5,011,484 | 4/1991 | Breard . |
| 5,015,247 | 5/1991 | Michelson . |
| 5,042,982 | 8/1991 | Harms et al. . |
| 5,047,029 | 9/1991 | Aebi et al. . |
| 5,084,048 | 1/1992 | Jacob et al. . |
| 5,084,049 | 1/1992 | Asher et al. . |
| 5,090,854 | 2/1992 | Hafeli et al. ............ 411/186 |
| 5,092,867 | 3/1992 | Harms et al. . |

FOREIGN PATENT DOCUMENTS 22178323  2/1987  United Kingdom .

*Primary Examiner*—David Isabella
*Assistant Examiner*—Debra S. Brittingham
*Attorney, Agent, or Firm*—Blakely, Sokoloff, Taylor & Zafman

[57] ABSTRACT

A spinal implant that has a rod that connects and stabilizes the vertebrae of a vertebral column. The implant has screws that are attached to the vertebrae. Each screw has a clamp with a first bore that allows the clamp to be placed over the screw. The first bore of the clamp is larger than the major diameter of the screw, so that the clamp can float about the screws. The clamps each have a second bore perpendicular to the first bore, adapted to receive and hold the rod. Integrally formed with the second bore of each clamp are a pair of flanges. When the flanges are deflected inward, the clamp "grabs" the rod. The clamp is placed on a hexagonally shaped shoulder of the screw. A nut is fastened onto the opposite side of the clamp, such that the flanges are pressed between the shoulder and the nut. The diameter of the second bore and rod are approximately the same so that a small deflection of the flanges produces a large clamping force on the rod.

20 Claims, 2 Drawing Sheets

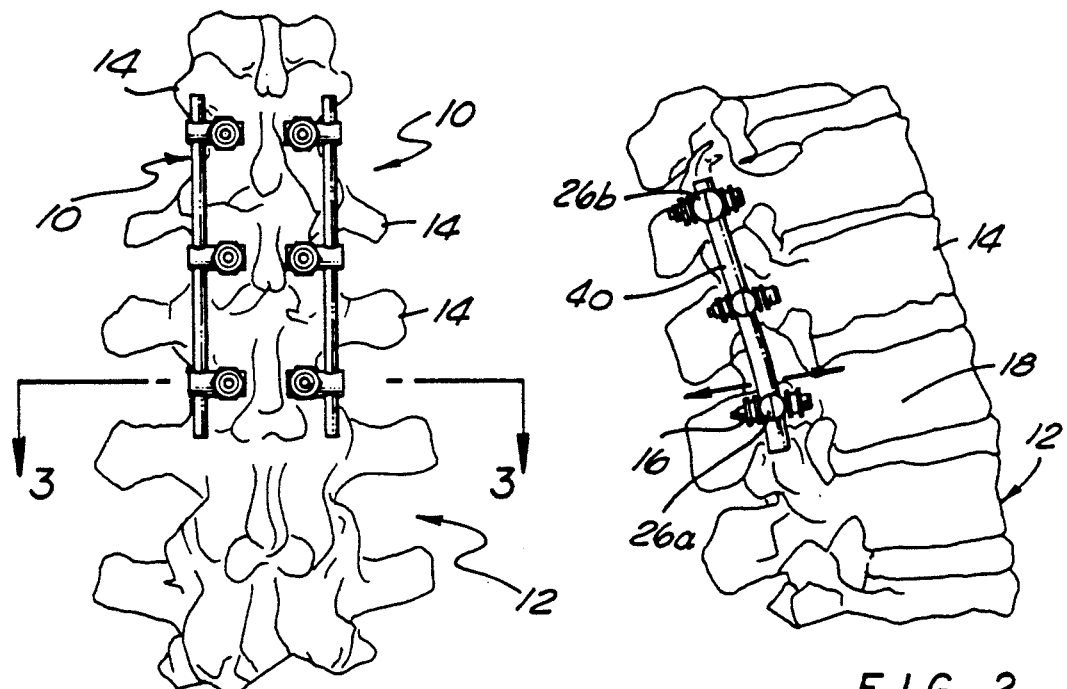
FIG. 1
FIG. 2
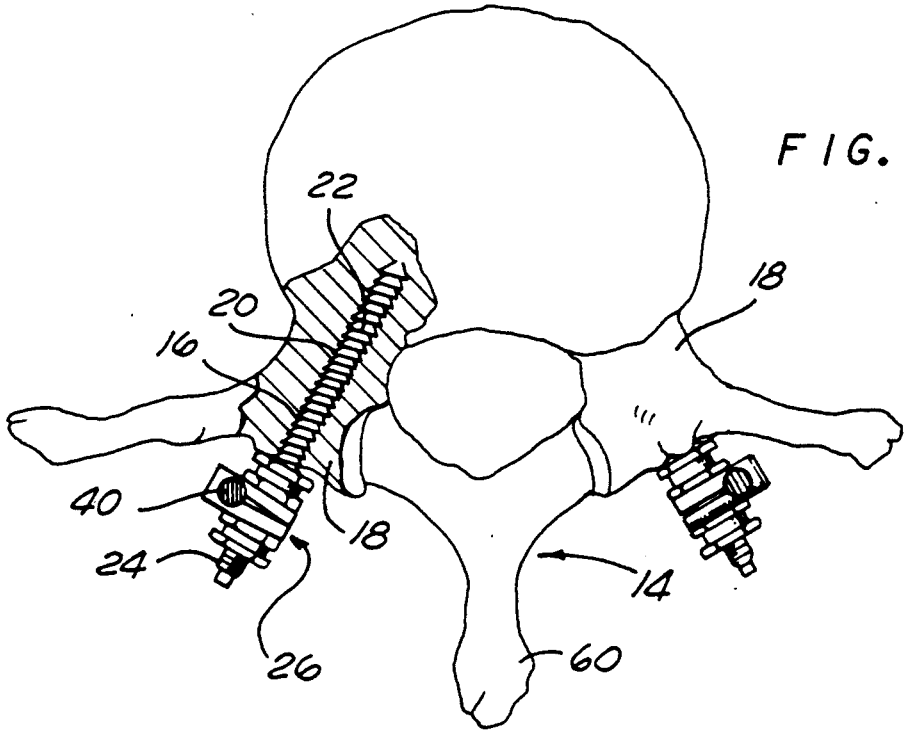
FIG. 3

SPINAL IMPLANT SYSTEM AND A METHOD FOR INSTALLING THE IMPLANT ONTO A VERTEBRAL COLUMN

BACKGROUND OF THE INVENTION

This application is a continuation-in-part of application Ser. No. 719,191, filed on Jun. 21, 1991.

FIELD OF THE INVENTION

This invention relates to a spinal implant that holds and stabilizes the vertebrae of a vertebral column.

DESCRIPTION OF THE RELATED ART

When the vertebrae of a backbone are fused together it is critical that the vertebrae are in proper orientation with respect to each other and remain that way throughout the fusing process. One present method of insuring alignment is to attach a plate to the vertebrae, which holds the skeletal members in position during the fusing process. The plate is attached to each vertebrae by screws that are screwed into the pedicle of each vertebra. The plate has holes or slots that fit over the screws, wherein two nuts are located on each side of the plate to fasten the same to the screws.

Because the spine is curved, the plate must have a radius to conform to the shape of the vertebral column. To create such a curvature, the plate is usually bent by the surgeon in the operating room before the installation of the implant. The formation of the plate and the assembly of the implant is inexact, such that the plate and screws are typically at an angle to each other. This lack of perpendicularity causes the nuts to engage the member in an uneven manner, wherein it has been found that the nuts would break at the threads of the screws after installation.

Another type of spinal implant includes screws that have a lug at one end. The screws are screwed into the pedicles and a preformed rod is inserted through the lugs to connect the vertebrae together. The hole diameter of the lug is larger than the diameter of the rods, so that absolute perpendicularity between the two members is not required. The rod is secured to the screws by set screws which are inserted through the lugs and engage the rod. Set screws are not the most rigid means of attachment, wherein there is a possibility that the rod will disengage from the screws and allow the vertebrae to move relative to each other. Therefore it would be desirable to have an easy to install rigid spinal implant, that would not require perpendicularity between the screws and the tie rod.

SUMMARY OF THE INVENTION

The present invention is a spinal implant that has a rod that connects and stabilizes the vertebrae of a vertebral column. The implant has screws that are attached to the pedicles of the vertebrae. Each screw has a clamp with a first bore that allows the clamp to be placed over the screw. The first bore of the clamp is larger than the major diameter of the screw, so that the clamp can float about the screw. The oversized first bore compensates for a lack of perpendicularity between the clamp and rod, so that a nonconforming rod may be installed onto the spine.

The clamps each have a second bore which is essentially perpendicular to the first bore. The second bore is adapted to receive and hold the rod. Integrally formed with the second bore of each clamp are a pair of flanges. When the flanges are deflected inward, the clamp "grabs" the rod. The clamp is placed on a hexagonal shaped shoulder of the screw. A nut is fastened onto the opposite side of the clamp, such that the flanges are pressed between the shoulder and nut. The diameter of the second bore and rod are approximately the same, so that a small deflection of the flanges produces a large clamping force on the rod.

Therefore, it is an object of this invention to provide a spinal implant that is rigidly secured to the vertebral column and does not require perpendicularity between the rod and screws.

BRIEF DESCRIPTION OF THE DRAWINGS

The objects and advantages of this invention will become more readily apparent to those skilled in the art after reviewing the following detailed description and accompanying drawings, wherein:

FIG. 1 is a posterior view of a vertebral column, showing a pair of spinal implants of the present invention attached to the vertebral column;

FIG. 2 is a lateral view of a portion of a vertebral column, showing a spinal implant attached to the vertebral column;

FIG. 3 is an axial view of an vertebra, showing screws embedded into the body of the vertebra;

DETAILED DESCRIPTION OF THE INVENTION

Figure 4:
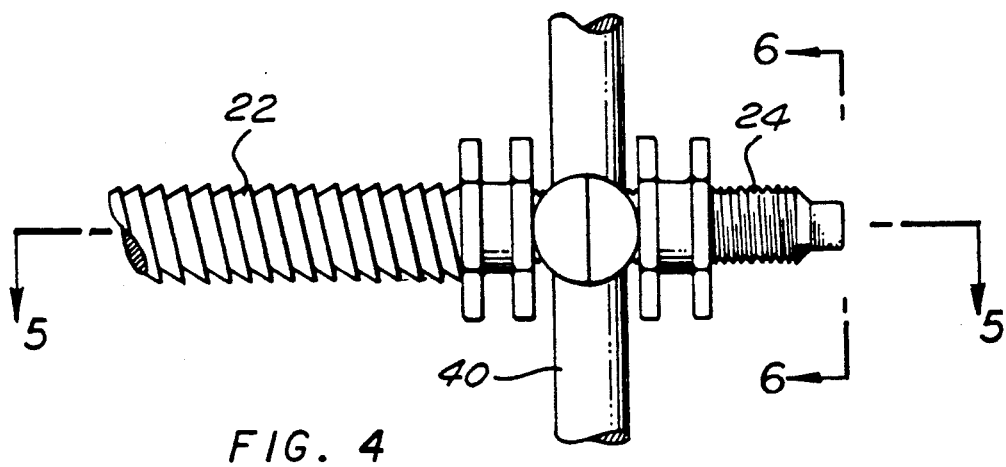
FIG. 4 is a side view of a portion of the spinal implant, showing nuts in contact with a clamp.

Referring to the drawings more particularly by reference numbers, FIG. 1 shows spinal implants 10 of the present invention attached to a vertebral column 12 comprising a plurality of vertebra 14. The implants 10 shown are attached to three vertebra 14 that can then fuse together. Although the attachment of three vertebrae are shown, it is to be understood that the implant 10 can vary in size such that any number of vertebrae can be held in place. It further being understood that one or two implants can be attached to the vertebrae, it being preferable to use two implants for greater stability.

FIGS. 2-6 more clearly shows the particular elements of the implant 10, wherein screws 16 are attached to the pedicles 18 of each vertebra 14. To attach one of the screws 16, a pedicle 18 is drilled with a bit having a diameter significantly smaller than the diameter of the screw 16. The drill bit is left in the bone while the bone is X-rayed, to determine if the tapped hole is of the proper depth and location in the pedicle 18. The drill bit is then removed and a hole 20 is drilled into the pedicle 18. The diameter of the hole 20 is no greater than the minor thread diameter of a first threaded portion 22 of the screw 16, such that the screw 16 can be screwed into tight engagement with the pedicle 18. The first threaded portion 22 typically has a course thread to increase the contact area between the threads and the bone. The screw 16 has a threaded second portion 24 that extends out from the pedicle 18, to allow a clamp 26 to be attached to each screw 16.

Figure 5:
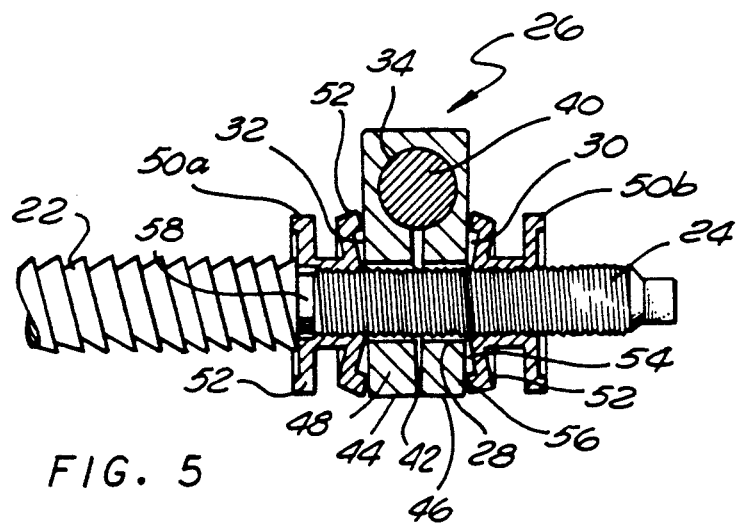
FIG. 5 is a cross-sectional view of FIG. 4, taken at line 5—5, showing the screw inserted through a clamp bore and annular flanges of the nuts.
Figure 6:
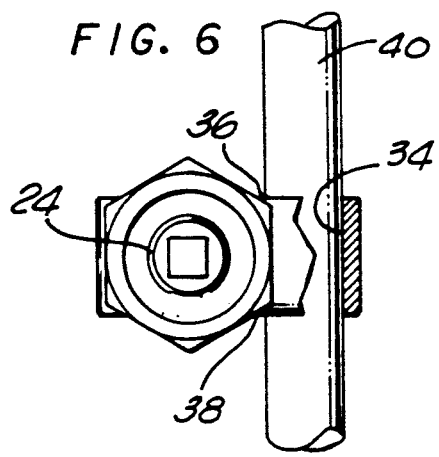
FIG. 6 is a side view of FIG. 4, taken at line 6—6, showing a portion of the clamp broken out to reveal how the rod extends through a bore of the clamp.

As more clearly shown in FIG. 5, the clamp 26 has a first bore 28 extending from a top surface 30 to a bottom surface 32 that allows the screw 16 to extend through the clamp 26. The clamp 26 has a second bore 34 that extends from a first side 36 to a second side 38, wherein the second bore 34 is essentially perpendicular to the first bore 28. Inserted through the second bore 34 of each clamp is a rod 40. The rod 40 creates a structural attachment between the clamps 26 and screws 16, such that when the rod 40 is clamped in place, the vertebrae 14 cannot move relative to each other. The rod 40 is preferably constructed from a metal and has a stiffness great enough to prevent excessive movement of the vertebrae 14 during the fusing process. A slit 42 extends from one end 44 of the clamp 26 to the second bore 34. The slit 42, clamp end 44 and top 30 and bottom 32 surfaces define first 46 and second 48 flanges, respectively. An inward deflection of the flanges causes the clamp 26 to grasp the rod 40. In the preferred embodiment, the rod 40 and second bore 34 are approximately the same diameter so that a small deflection of the flanges 46 and 48, produces a large clamping force. The tolerances of the rod 40 and second bore 34 are preferably very close, wherein it is preferable to ream the second bore 34.

Each screw 16 has a first 50a and second nut 50b that threadably engage the threaded second portion 24 of the screw 16. The nuts 50 can be turned such that they engage and deflect both the first 46 and second flanges 48, so that the clamp 26 is pressed onto the rod 40. The incorporation of the flanges 46 and 48 into the clamp 26, provide an easy means of rigidly attaching and detaching the rod 40, by tightening or loosening the nuts 50.

It is preferable that the nuts 50 have annular flanges 52 on the ends thereof, that have counterbores 54 to define an annular rim 56 that engages the clamp 26. As shown in FIG. 5 the nuts can be turned until the annular nut flanges 52 deflect, locking the nuts 50 against the clamp 26. It is preferable to have annular flanges 52 on both ends of each nut 50a and 50b so that the nuts 50 are reversible. The second annular flanges 52 also provide a better means to grasp the nuts 50.

In the preferred embodiment the first bore 28 and the second threaded portion 24 are of such dimensions to allow the clamp 26 to rotate 20° to 30° about an axis perpendicular to the longitudinal axis of the screw 16. The movement of the clamp 26 relative to the screw 16 allows a rod 40 to be installed, that is not perpendicular to the screws 16 and does not conform exactly with the vertebral column 12. The screws 16 may have a thread relief 58 between threaded portions 22 and 24.

To attach and use the spinal implant 10, the screws 16 are attached to the vertebrae 14 that are to be fused as described above. A first nut 50a is screwed onto the second threaded portion 24 of each screw 16. The first nut 50a is preferably turned until the nut 50a engages the first threaded portion 22 of the screw. The rods 40 are then bent to a radius approximating the curvature of the vertebral column 12 and inserted into the second bore 34 of the clamps 26. The clamps 26 and rod 40 are placed onto the screws 16 by inserting the second threaded portions 24 through the first bore 28 of the clamps 26. A second nut 50b is screwed onto the second threaded portion 24, wherein the first and second nuts are turned until the second nut 50b engages the top surface 30 of the clamp 26, and the first nut 50a engages the bottom surface 32, see FIG. 5. The flanges 46 and 48, are deflected by the nuts 50a and 50b, such that the clamp 26 securely grasp and holds the rod 40 in place.

Figure 7:
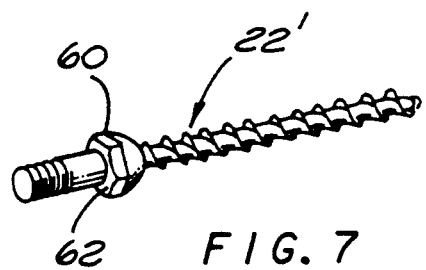
FIG. 7 is a perspective view of an alternative embodiment of the present invention.

FIG. 7 shows an alternate embodiment of the present invention. Instead of the nut 50a, the screw 22' may have a shoulder 60 with an essentially flat first surface 62. The shoulder 60 is hexagonally shaped so that the screw 22' can be turned into the vertebra 14. The clamp 26 is placed on top of the shoulder 60 so that the flange 48 is contiguous with the first surface 62. The nut 50b is placed on top of the clamp 26 and tightened until the flanges are deflected and the rod 40 is secured to the clamp 26. The integration of the shoulder 60 into the screw 22', simplifies the installation of the implant, wherein only the nut 50b need be manipulated by the user.

While certain exemplary embodiments have been shown and described in the above description and accompanying drawings, it is to be understood that such embodiments are merely illustrative of, and not restrictive on the broad invention, and that this invention not be limited to the specific constructions and arrangements shown and described, since various other modifications may occur to those ordinarily skilled in the art.

What is claimed is:

1. A spinal implant for stabilizing a vertebrae of a vertebral column, wherein the vertebral column has a curvature along at least one vertical axis and each vertebra has a pair of pedicles, comprising:
   at least two cylindrical clamps each having a first flange, and a second flange separated from said first flange by a slit, said clamps further having a first bore that extends through said first and second flanges, said first and second flanges both having cylindrical outer surfaces and a second bore essentially perpendicular to said first bore;
   a rod adapted to be inserted into and extend through said second bores;
   at least two screws, each said screw having a first threaded portion adapted to be attached to the pedicle of a vertebra and a second threaded portion adapted to extend through said first bore, each said screw further having a shoulder between said first and second threaded portions adapted to engage said cylindrical outer surface of said second flange of said clamp; and
   at least two nuts adapted to be threaded onto said second portion of said screws, each screw having one nut adapted to engage said outer cylindrical surface of said first flange of said clamp wherein said cylindrical clamps can rotate about an axis perpendicular to a longitudinal axis of said screw without interference between said cylindrical clamp and said shoulders and said nuts.

2. The spinal implant as recited in claim 1, wherein said shoulder is hexagonal in shape.

3. The spinal implant as recited in claim 1, wherein said rod has an outer diameter and said second bore has an inner diameter that are approximately the same diameter.

4. The spinal implant as recited in claim 1, wherein said nuts each have an annular flange adapted to engage said first flanges, said annular flanges being constructed such that said annular flanges deflect when said nuts are turned into tight engagement with said clamp, locking said nut onto said clamp.

5. The spinal implant as recited in claim 1, wherein said nuts each have two annular flanges adapted to engage said first flanges, said annular flanges being constructed such that said annular flanges deflect when said nuts are turned into tight engagement with said clamp, locking said nuts onto said clamp.

6. The spinal implant as recited in claim 1, wherein said second threaded portion of said screw has a predetermined outer diameter and said first bore has a predetermined inner diameter larger than said outer diameter of said screw enabling said clamp to rotate up to 30° about an axis perpendicular to the longitudinal axis of said screw.

7. A spinal implant for stabilizing a vertebrae of a vertebral column, wherein the vertebral column has a curvature along at least one vertical axis and each vertebra has a pair of pedicles, comprising:
   at least two cylindrical clamps each having a first flange, and a second flange separated from said first flange by a slit, said clamps further having a first bore that extends through said first and second flanges, said first and second flanges both having cylindrical outer surfaces and a second bore essentially perpendicular to said first bore;
   a rod adapted to be inserted into and extend through said second bores;
   at least two screws, each said screw having a first threaded portion adapted to be attached to the pedicle of a vertebra and a second threaded portion adapted to extend through said first bore, each said screw further having a hexagonally shaped shoulder between said first and second threaded portions, said second threaded portion having a predetermined outer diameter and said first bore having a predetermined inner diameter larger than said outer diameter of said screw enabling said clamp to rotate up to 30° about an axis perpendicular to the longitudinal axis of said screw and shoulders being adapted to engage said cylindrical outer surface of second flanges of said clamps; and
   at least two nuts adapted to be threaded onto said second portion of said screws, each screw having one nut with an annular flange adapted to engage said cylindrical outer surface of said first flange of said clamp such that said annular flange deflects to lock said first nut onto said clamp wherein said cylindrical clamps can be rotated about an axis perpendicular to a longitudinal axis of said screw without interference between said cylindrical clamp and said shoulders and said nuts.

8. A spinal implant for stabilizing the vertebrae of a vertebral column, wherein the vertebral column has a curvature along at least one vertical axis and each vertebra has a first and second pedicle, comprising:
   at least two cylindrical clamps, each said clamp having a first flange and a second flange separated from said first flange, by a slit, said clamps further having a first bore that extends through said first and second flanges, said first and second flanges both having cylindrical outer surfaces and a second bore essentially perpendicular to said first bore;
   a rod that extends through said second bores, said rod having a radius approximating the curvature of the vertebral column;
   at least two screws, each said screw having a first threaded portion attached to the first pedicle of a vertebra and a second threaded portion that extends through said first bore such that each said screw has a clamp attached thereto, each said screw further having a shoulder that engages said cylindrical outer surface of said second flange of said clamp;
   at least two nuts attached to said second portion of said screws, each screw having one nut engaging said cylindrical outer surface of said first flange of said clamp such that said first flange is deflected, said cylindrical clamps can be rotated about an axis perpendicular to a longitudinal axis of said screws without interference between said cylindrical clamps and said shoulders and said nuts.
   whereby said nut and said shoulder deflect said first and second flanges so that said clamp is pressed onto said rod such that said rod is held in firm engagement by said clamp.

9. The spinal implant of claim 8, further comprising a second set of clamps, screws, rod and nuts assembled as described in claim 8, said screws of said second set being attached to the second pedicles of the vertebrae, whereby there are two spinal implants attached to the vertebral column.

10. The spinal implant as recited in claim 8, wherein said rod has an outer diameter and said second bore has an inner diameter that are approximately the same diameter.

11. The spinal implant as recited in claim 8, wherein said nuts each have an annular flange that engages said first flanges, said annular flanges being constructed such that said annular flanges deflect when said nuts are turned into tight engagement with said clamp, locking said nuts onto said clamp.

12. The spinal implant as recited in claim 8, wherein said nuts each have two annular flanges, wherein one of said two annular flanges engages said first flanges, said annular flanges being constructed such that said annular flanges deflect when said nuts are turned into tight engagement with said clamp, locking said nuts onto said clamp.

13. The spinal implant as recited in claim 8, wherein said second threaded portion of said screw has a predetermined outer diameter and said first bore has a predetermined inner diameter larger than said outer diameter of said screw enabling said clamp to rotate up to 30° about an axis perpendicular to the longitudinal axis of said screw.

14. A method for attaching a spinal implant to a vertebrae of a vertebral column to stabilize the vertebrae, wherein the vertebral column has a curvature along at least one vertical axis and each vertebra has a first and second pedicle, comprising the steps of:
   providing;
      at least two cylindrical clamps each having a first flange, and a second flange separated from said first flange by a slit, said clamps further having a first bore that extends through said first and second flanges, said first and second flanges both having cylindrical outer surfaces and a second bore essentially perpendicular to said first bore;
      a rod adapted to be inserted into and extend through said second bores;
      at least two screws, each said screw having a first threaded portion adapted to be attached to the pedicle of a vertebra and a second threaded portion adapted to extend through said first bore, each said screw further having a shoulder between said first and second threaded portions adapted to engage said cylindrical outer surface of said second flange of said clamp;

at least two nuts adapted to thread onto said second threaded portion of said screws, each screw having one nut adapted to engage said cylindrical outer surface of said first flange of said clamp;

attaching said screws to the first pedicle of at least two vertebra such that each vertebra has one screw;

inserting said rod into said second bores of said clamps;

placing said clamps and said rod onto said screws such that said second portion of said screws is inserted through said first bores of said clamps, said cylindrical clamps being capable of rotation about a longitudinal axis of said screws without interference between said cylindrical clamps and said shoulder and said nuts;

screwing said nuts onto said second threaded portion of said screws, such that each screw has one nut, each said nut being screwed onto said second threaded portion until said nut engages said first flange of said clamp and said second flange of said clamp engages said shoulder; and tightening said nut of each screw such that said first and second flanges are deflected, pressing said clamp onto said rod, whereby said rod is securely fastened to the vertebrae to hold the vertebrae in place.

15. The method as recited in claim 14, further comprising the step of bending said rod before said clamp and said rod are placed on said second threaded portion, such that said rod approximates the curvature of the vertebral column.

16. The method as recited in claim 14, further comprising providing a second set of clamps, rod, screws and nuts and attaching said screws of said second set to the second pedicle of at least two vertebra and following the steps recited in claim 14, whereby there are two spinal implants attached to the vertebral column.

17. The method as recited in claim 14, wherein said first rod has an outer diameter and said second bore has an inner diameter that are approximately the same diameter.

18. The method as recited in claim 14, wherein said second nuts each have an annular flange adapted to engage said first flanges, said annular flanges being constructed such that said annular flanges deflect when said nuts are turned into tight engagement with said clamp, locking said nuts onto said clamp.

19. The method as recited in claim 14, wherein said second nuts each have two annular flanges adapted to engage said first flanges, said annular flanges being constructed such that said annular flanges deflect when said nuts are turned into tight engagement with said clamp, locking said nuts onto said clamp.

20. The method as recited in claim 14, wherein said second threaded portions of said screw has a predetermined outer diameter and said first bore has a predetermined inner diameter larger than said outer diameter of said screws enabling said clamp to rotate up to 30° about an axis perpendicular to the longitudinal axis of said screw.

* * * * *